United States Patent [19]

Sitzmann et al.

[11] Patent Number: 4,705,899

[45] Date of Patent: Nov. 10, 1987

[54] 1:3 "MIXED" POLYNITROETHYL ORTHOCARBONATES FROM TRIS(2-FLUORO-2,2-DINITROETHOXY)-METHYL TRICHLOROMETHYL DISULFIDE

[75] Inventors: Michael E. Sitzmann, Adelphi; William H. Gilligan, Fort Washington, both of Md.

[73] Assignee: The United States of America as represented by the Secretary of the Navy, Washington, D.C.

[21] Appl. No.: 467,713

[22] Filed: Feb. 18, 1983

[51] Int. Cl.$^4$ .................... C07C 43/32; C07C 43/317; C06B 25/00

[52] U.S. Cl. ...................................... 568/590; 149/88; 568/22; 549/556

[58] Field of Search ......................................... 568/590

[56] References Cited

U.S. PATENT DOCUMENTS 3,306,939  2/1967  Hill et al. ............................. 568/590
3,388,147  6/1968  Kamlet et al. ....................... 568/590

Primary Examiner—Howard T. Mars

Attorney, Agent, or Firm—Kenneth E. Walden; Roger D. Johnson

[57] ABSTRACT

1:3 "mixed" orthocarbonates of the formula

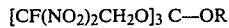

wherein R is
—$CH_2C(NO_2)_3$,
—$CH_2C(NO_2)_2CH_3$,
—$CH_2CH_2NO_2$,
—$CH_2C(NO_2)_2CH_2OH$,
—$CH_2C(NO_2)_2CH_2OC[OCH_2CF(NO_2)_2]_3$,
—$CH_2C(NO_2)_2CH_2OCH_2OCH_2C(NO_2)_2CH_2OH$,
—$CH_2C(NO_2)_2CH_2OCH_2OCH_2C(NO_2)_2CH_2OC$-$[OCH_2CF(NO_2)_2]_3$,
—$CH_2CF_3$,
—$CH_2CH_3$, and

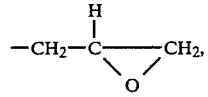

and a method of preparation.

10 Claims, No Drawings

1:3 "MIXED" POLYNITROETHYL ORTHOCARBONATES FROM TRIS(2-FLUORO-2,2-DINITROETHOXY)METHYL TRICHLOROMETHYL DISULFIDE

BACKGROUND OF THE INVENTION

This invention relates to organic orthocarbonates and more particularly, to organic polynitroorthocarbonates.

In the early 1950's, M. E. Hill and co-workers at the Naval Ordnance Laboratory, found that certain nitroalcohols would react with carbon tetrachloride in the presence of anhydrous ferric chloride to yield

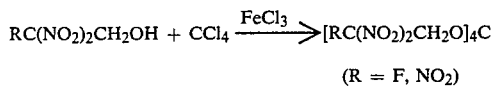

(R = F, NO$_2$)

symmetrical orthocarbonates. (e.g., See U.S. Pat. No. 3,306,939, entitled "Orthoesters of 2,2,2-Trinitroethanol," which issued to Marion E. Hill on Feb. 28, 1967.) However, the reaction is of very limited synthetic value for energetic orthocarbonates as only three nitroalcohols (2-fluoro-2,2-dinitroethanol, 2,2,2-trinitroethanol and 2,2-dinitropropane-1,3-diol) have been successfully used. With other nitroalcohols side reactions predominate and the principal product is the carbonate. Another drawback to Hill's method is that only symmetrical and no "mixed" orthocarbonates can be prepared. Heretofore no method has been available for the synthesis of 1:3 "mixed" orthocarbonates.

SUMMARY OF THE INVENTION

Accordingly, an object of this invention is to provide novel organic compounds.

Another object of this invention is to provide new high energy, high density explosive materials.

A further object of this invention is to provide new melt castable explosives.

Yet another object of this invention is to provide new intermediates for the preparation of novel explosive compounds.

A still further object of the invention is to provide new high energy plasticizers.

Another object of this invention is to provide a new method of synthesizing novel explosives compounds.

These and other objects of this invention are accomplished by providing a 1:3 mixed orthocarbonate of the formula

[CF(NO$_2$)$_2$CH$_2$O]$_3$C—OR wherein R is
—CH$_2$C(NO$_2$)$_3$,
—CH$_2$C(NO$_2$)$_2$CH$_3$,
—CH$_2$CH$_2$NO$_2$,
—CH$_2$C(NO$_2$)$_2$CH$_2$OH,
—CH$_2$C(NO$_2$)$_2$CH$_2$OC[OCH$_2$CF(NO$_2$)$_2$]$_3$,
—CH$_2$C(NO$_2$)$_2$CH$_2$OCH$_2$OCH$_2$C(NO$_2$)$_2$CH$_2$OH,
—CH$_2$C(NO$_2$)$_2$CH$_2$OCH$_2$OCH$_2$C(NO$_2$)$_2$CH$_2$OC-[OCH$_2$CF(NO$_2$)$_2$]$_3$,
—CH$_2$CF$_3$,
—CH$_2$CH$_3$, or

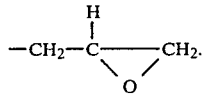

These orthocarbonates are prepared by the following reaction sequence:

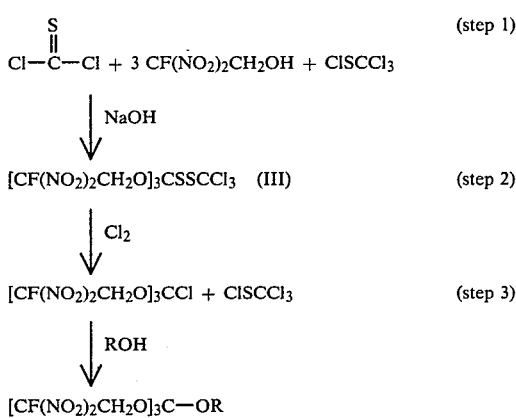

wherein R is as defined above.

The intermediate [CF(NO$_2$)$_2$CH$_2$O]$_3$CSSCCl$_3$ may also be prepared by the following reaction:

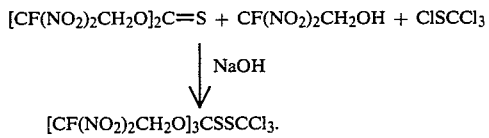

The orthoformates of this invention are useful as explosives and as energetic additives to explosives and propellants.

DETAILED DESCRIPTION OF THE PREFERRED EMBODIMENT

1:3 "mixed" orthocarbonates of the formula

[CF(NO$_2$)$_2$CH$_2$O]$_3$C—OR are produced by reaction of one mole of tris(2-fluoro-2,2-dinitroethyl)chloroorthoformate,

[CF(NO$_2$)$_2$CH$_2$O]$_3$CCl, with one mole of an alcohol of the formula ROH wherein R is
—CH$_2$C(NO$_2$)$_3$,
—CH$_2$C(NO$_2$)$_2$CH$_3$,
—CH$_2$CH$_2$NO$_2$,
—CH$_2$C(NO$_2$)$_2$CH$_2$OH,
—CH$_2$C(NO$_2$)$_2$CH$_2$OC[OCH$_2$CF(NO$_2$)$_2$]$_3$,
—CH$_2$C(NO$_2$)$_2$CH$_2$OCH$_2$OCH$_2$C(NO$_2$)$_2$CH$_2$OH,
—CH$_2$C(NO$_2$)$_2$CH$_2$OCH$_2$OCH$_2$C(NO$_2$)$_2$CH$_2$OC-[OCH$_2$CF(NO$_2$)$_2$]$_3$,
—CH$_2$CF$_3$,
—CH$_2$CH$_3$, and

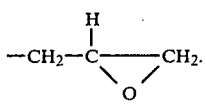

The tris(2-fluoro-2,2-dinitroethyl)chloroorthoformate, [CF(NO$_2$)$_2$CH$_2$O]$_3$C-Cl (I), is formed by the reaction of tris(2-fluoro-2,2-dinitroethoxy)methyl trichloromethyl disulfide, [CF(NO$_2$)$_2$CH$_2$O]$_3$CSSCl$_3$, with chlorine gas. The chloroorthoformate (I) can be isolated but since it is very reactive with moisture equally good or better results are usually obtained if it is treated in situ with the specific alcohol to produce the desired 1:3 mixed orthocarbonate. Examples 4 through 14 illustrate the conditions suitable for this step. In particular, 1,2-dichloroethane as a solvent and a reaction temperature of from 60° to 70° C. are preferred.

Di[tris(2-fluoro-2,2-dinitroethoxy)methyl]disulfide may be used in place of tris(2-fluoro-2,2-dinitroethoxy)methyl trichloromethyl disulfide in the above procedure for preparing tris(2-fluoro-2,2-dinitroethyl)-chloroothoformate. One mole of di[tris(2-fluoro-2,2-dinitroethoxy)methyl]disulfide reacts with the chlorine gas to form 2 moles of the chloroorthoformate under the conditions given above. The disulfide is prepared by the procedure given in Example 3.

If the alcohol (ROH) to be reacted with the [CF(NO$_2$)$_2$CH$_2$O]$_3$CCl is stable to chlorination, the chlorine gas may be fed into a mixture of alcohol and [CF(NO$_2$)$_2$CH$_2$O]$_3$CSSCl$_3$ (see examples 4 through 11). As [CF(NO$_2$)$_2$CH$_2$O]$_3$CCl is formed it can react with the alcohol. However, if the alcohol can react with chlorine, it may be added after the chloroformate has formed and the excess chlorine is removed and then reacted (see examples 12 through 14).

Example 1 illustrates the method of forming [CF(NO$_2$)$_2$CH$_2$O]$_3$CSSCCl$_3$ by reacting 2-fluoro-2,2-dinitroethanol, thiophosgene, and perchloromethylmercaptan in a 3:1:1 molar ratio in the presence of a base. Example 2 illustrates an alternative method of preparing [CF(NO$_2$)$_2$CH$_2$O]$_3$CSSCCl$_3$ from bis(2-fluoro-2,2-dinitroethyl thionocarbonate, 2-fluoro-2,2-dinitroethanol, and perchloromethylmercaptan in a 1:1:1 molar ratio in the presence of a base. In both instances a suitable inert solvent such as dichloromethane, 1,2-dichloroethane, or 1,1,2-trichloroethane may be used. A reaction temperature in the range of from −5° C. to 5° C. is preferred with 0° C. to 5° C. being more preferred. Also in both cases the base used is preferably a strong hydroxyl ion source such as aqueous KOH or NaOH. The base is added slowly at a rate such that the pH of the reaction mixture does not exceed 8. This is done to avoid the hydrolysis of thionocarbonates to carbonates which occurs in strongly basic solutions. Finally, a phase transfer catalyst is preferably used to speed up the reaction rate in both the above procedures.

Phase transfer catalysts such as benzyltriethylammonium chloride, tetrabutylammonium chloride, didodecyldimethylammonium bromide, or cetyltrimethylammonium chloride may be used. The phase transfer catalyst is not consumed by the reaction; therefore only a small amount, a few mole percent, of the phase transfer catalyst is required.

Good discussions on the use of phase transfer catalysts are presented by Charles M. Starks, "Phase Transfer Catalysts. I. Heterogeneous Reactions Involving Anion Transfer by Quaternary Ammonium and Phosphonium Salts," Journal of the American Chemical Society, Volume 93:1, Jan. 13, 1971, pages 195–199, and by Echehard V. Dehmlow, "Phase-Transfer Catalyzed Two-Phase Reactions in Preparative Organic Chemistry," Angew, Chem. internat Edit. volume 13 (1974)/No. 3, Pages 170–178, adapted in Chemtech, April 1975, pages 210–218.

The two procedures above for making tris(2-fluoro-2,2-dinitroethoxy)methyl trichloromethyl disulfide may be modified by substituting the 2-fluoro-2,2-dinitroethyl ester of trichloromethylsulfenic acid, CF(NO$_2$)$_2$CH$_2$OSCCl$_3$, for perchloromethylmercaptan. A procedure for making the ester is given in Example 15.

The bis(2-fluoro-2,2-dinitroethyl)thionocarbonate starting material may be produced by the method disclosed in U.S. Pat. No. 4,172,088, entitled "Bis(2-fluoro-2,2-dinitroethyl)thionocarbonate and a Method of Preparation," which was issued to Angres et al on Oct. 23, 1979, herein incorporated by reference.

To more clearly illustrate this invention, the following examples are presented. It should be understood, however, that these examples are presented merely as a means of illustration and are not intended to limit the scope of the invention in anyway.

EXAMPLE 1

Tris(2-fluoro-2,2-dinitroethoxy)methyl trichloromethyl disulfide (III) from thiophosgene

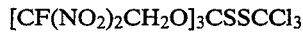

[CF(NO$_2$)$_2$CH$_2$O]$_3$CSSCCl$_3$

A well-stirred mixture of 40 g (0.26 mol) of 2-fluoro-2,2-dinitroethanol in 110 ml of methylene chloride and 2 g of tetrabutyl ammonium chloride in 100 ml of water was cooled in an ice-salt bath to 0° C. A solution of 6.60 g (0.05 mol) of 85% thiophosgene [from Aldrich Chemical Co.; contains 15% carbon tetrachloride] and 12.1 g (0.065 mol) of perchloromethylmercaptan in 30 ml of methylene chloride was added all at once followed by the dropwise addition of 11.2 ml of 50% aqueous sodium hydroxide keeping the temperature at 0° to 4° C. The reaction solution was then stirred at 0° C. for 40 minutes keeping it slightly basic by the occasional addition of a few drops of 50% sodium hydroxide. The methylene chloride layer was separated, dried (MgSO$_4$), and the volatiles were removed to give 45.8 g of an oily residue which was dissolved in 60 ml of chloroform. Cooling to −20° C. gave 1.55 g (6%) of di[tris(2-fluoro-2,2-dinitroethoxy)methyl]disulfide (XVI). Hexane was added to the chloroform mother liquor until it began to cloud at room temperature. It was then treated with charcoal and filtered through a silica gel pad (40 g silica gel 60; pad is 2.5 inch diameter and 1 inch deep). The pad was washed with 4×50 ml of chloroform-hexane (3:2). Additional hexane was added to the filtrate (to give 350 ml total volume) which was then cooled in dry ice-acetone to give 23.0 g (70%) of white solid, mp 52°–55° C. Recrystallization by dissolving in 50 ml chloroform, adding 75 ml hexane and cooling to −20° gave 21.2 g (65%), mp 55°–57° C.; H-NMR(CDCl$_3$)δ 4.84(d); mass spectrum (C.I.): m/e 503, 471.

Anal. Calcd. for C$_8$H$_6$N$_6$F$_3$Cl$_3$S$_2$O$_{15}$: C, 14.70; H, 0.93; N, 12.86; F, 8.72; Cl, 16.27; S, 9.81. Found: C, 14.59; H, 1.07; N, 12.64; F, 8.64; Cl, 16.32; S, 9.61.

EXAMPLE 2

Tris(2-fluoro-2,2-dinitroethoxy)methyl trichloromethyl disulfide (III) from Bis(2-fluoro-2,2-dinitroethyl)thionocarbonate

[CF(NO$_2$)$_2$CH$_2$O]$_3$CSSCCl$_3$

A solution of 17.5 g (0.05 mol) of bis(2-fluoro-2,2-dinitroethyl)thionocarbonate, 17.7 g (0.115 mol) of 2-fluoro-2,2-dinitroethanol and 12.1 g (0.065 mol) of perchloromethylmercaptan in 110 ml of methylene chloride was stirred vigorously in an ice-salt bath. A solution of 2 g of tetrabutylammonium chloride in 75 ml of water was added followed by the dropwise addition of 6 ml of 50% aqueous sodium hydroxide with cooling at 2° to 5° C. The reaction solution was kept slightly basic at 0° C. for 20 minutes by occasional addition of a few drops of 50% sodium hydroxide. Workup (same as in above experiment) gave 2.79 g (11%) of di[tris(2-fluoro-2,2-dinitroethoxy)methyl]disulfide (XVI) and 28.3 g (86%) of tris(2-fluoro-2,2-dinitroethoxy)methyl trichloromethyl disulfide (III), mp 52°–55° C. Recrystallization gave 26.05 g (80%), mp 55°–57° C.

A similar run starting with 42 g (0.12 mol) of the thionocarbonate, 22.4 g (0.12 mol) of perchloromethylmercaptan and 24 g (0.156 mol) of fluorodinitroethanol gave 8.4 g (14%) of di[tris(2-fluoro-2,2-dinitroethoxy)methyl]disulfide (XVI) and 55.0 g (70%) of tris(2-fluoro-2,2-dinitroethoxy)methyl trichloromethyl disulfide (III), mp 55°–57° C.

EXAMPLE 3

Di[tris(2-fluoro-2,2-dinitroethoxy)methyl]disulfide (XVI)

[(CF(NO$_2$)$_2$CH$_2$O]$_3$CSSC[OCH$_2$CF(NO$_2$)$_2$]$_3$

A solution of 1.96 g (0.003 mol) of tris(2-fluoro-2,2-dinitroethoxy)methyl trichloromethyl disulfide, 1.05 g (0.003 mol) of bis(2-fluoro-2,2-dinitroethyl)thionocarbonate and 0.6 g (0.004 mol) of 2-fluoro-2,2-dinitroethanol in 10 ml of methylene chloride was cooled in an ice-bath. Tetrabutyl ammonium chloride (0.3 g) in 6 ml of water was added followed by the dropwise addition of 0.40 g of 50% sodium hydroxide (diluted with 2 ml of water) with the temperature at 0° to 3° C. The methylene chloride layer contained solid precipitate which dissolved upon warming. Removal of the methylene chloride gave a residue which was stirred with 15 ml of chloroform and then cooled to −20° C. to give 1.44 g (48%) of white solid, mp 130°–133° C. Recrystallization from acetone-chloroform gave mp 134°–135° C.;

H-NMR[(CD$_3$)$_2$C=O]: δ5.30(d); mass spectrum (C.I.) m/e 471.

Anal. Calcd. for C$_{14}$H$_{12}$N$_{12}$F$_6$S$_2$O$_{30}$: C 16.71; H, 1.20; N, 16.70; F, 11.33, S, 6.37. Found: C, 16.54; H, 1.15; N, 16.13; F, 11.43; S, 6.14.

EXAMPLE 4

Tris(2-fluoro-2,2-dinitroethyl)chloroorthoformate(I)

[CF(NO$_2$)$_2$CH$_2$O]$_3$CCl

A solution of 1.0 g of di[tris(2-fluoro-2,2-dinitroethoxy)methyl]disulfide (XVI) in 4 ml of dry 1,2-dichloroethane and 3 ml of dry acetonitrile was treated with dry chlorine gas for 5 hours at ambient temperature. The volatiles were removed with a stream of nitrogen and gentle heating to give an oil which crystallized in the refrigerator overnight. Recrystallization from dry benzene-hexane gave crystals, mp 69°–72° C. The crystals are very hygroscopic, turning rapidly to a liquid if exposed to moist air. Elemental analysis showed the crystals contained no sulfur but the sensitivity of the crystals to moisture prevented a satisfactory analysis for other elements. TLC (toluene as developer) showed only bis(2-fluoro-2,2-dinitroethyl)carbonate and 2-fluoro-2,2-dinitroethanol, the expected products of hydrolysis of the chloroorthoformate (I) on the TLC plate.

Tris(2-fluoro-2,2-dinitroethyl)chloroorthoformate (I) can also be prepared by chlorinating tris(2-fluoro-2,2-dinitroethoxy)methyl trichloromethyldisulfide (III) at 60° C. in dichloroethane for 2 hours. The volatiles are removed with a stream of nitrogen and the perchloromethylmercaptan byproduct is washed away with hexane leaving tris(2-fluoro-2,2-dinitroethyl)-chloroorthoformate (I) behind as a white solid.

EXAMPLE 5

Tris(2-fluoro-2,2-dinitroethyl)(2,2,2-trinitroethyl)orthocarbonate (VI)

[CF(NO$_2$)$_2$CH$_2$O]$_3$C—O—CH$_2$C(NO$_2$)$_3$,

A solution of 2.58 g (0.0142 mol) of 2,2,2-trinitroethanol and 4.64 g (0.0071 mol) of tris(2-fluoro-2,2-dinitroethoxy)methyl trichloromethyl disulfide in 10 ml of 1,2-dichloroethane was treated with chlorine gas at 60°–70° C. for 2.5 hours. The solution was concentrated (approximately 5 ml of solvent was removed with a stream of nitrogen) and held at 60°–70° C. for 72 hours. The cooled reaction mixture was diluted with hexane and the product was washed with water to give 4.16 g of solid, mp 105°–115° C. Crystallization from chloroform gave 3.73 g (81%), mp 117°–118° C.; H-NMR (CDCl$_3$): δ 7.25(s), 4.69(d).

Anal. calcd for C$_9$H$_8$N$_9$F$_3$O$_{22}$: C, 16.60, H, 1.24; N, 19.36; F, 8.75. Found: C, 16.78; H, 1.16; N, 19.25; F, 8.93.

EXAMPLE 6

Tris(2-fluoro-2,2,2-dinitroethyl)(2,2-dinitropropyl)orthocarbonate (VII)

[CF(NO$_2$)$_2$CH$_2$O]$_3$C—O—CH$_2$C(NO$_2$)$_2$CH$_3$,

A solution of 4.2 g (0.028 mol) of 2,2-dinitropropanol and 6.53 g (0.01 mol) of tris(2-fluoro-2,2-dinitroethoxy)methyl trichloromethyl disulfide in 20 ml of dry 1,2-dichloroethane was treated with chlorine gas at 60°–65° C. for 2 hours. The solution was heated at 60°–65° C. for an additional 21 hours before the solvent was removed and the residue washed with hexane and water. The solid obtained was crystallized from chloroform to give 5.80 g (93%), mp 116°–117.5° C.; H-NMR(CDCl$_3$): δ 4.66(d), 4.38(s), 2.22(s); IR(KBr): 1605, shoulder at 1580(NO$_2$)cm$^{-1}$.

Anal. calcd. for C$_{10}$H$_{11}$N$_8$F$_3$O$_{20}$: C, 19.36; H, 1.79; N, 18.07; F, 9.19. Found: C, 19.41; H, 1.82; N, 18.03; F, 9.39.

EXAMPLE 7

Tris(2-fluoro-2,2-dinitroethyl)(2-nitroethyl)orthocarbonate (VIII).

[CF(NO$_2$)$_2$CH$_2$O]$_3$C—O—CH$_2$CH$_2$NO$_2$

A solution of 4.57 g (0.007 mol) of tris(2-fluoro-2,2-dinitroethoxy)methyl trichloromethyl disulfide and 0.76 g (0.0084 mol) of 2-nitroethanol in 15 ml of dry 1,2-dichloroethane was treated with chlorine gas at 60°-65° C. for 2 hours. The reaction solution was held at 60°-65° C. for an additional 5 hours before the volatiles were removed and the residue was washed with hexane and then with water to give 3.86 g (98%), mp 85°-88° C. Crystallization from chloroform yielded 3.59 g (91%), mp 89°-91° C.; H-NMR(CD$_2$Cl$_2$): δ 4.74 (d), 4.61-4.57(m), 4.18-4.11(m); IR(KBr): 1605, 1560(NO$_2$)cm$^{-1}$.

Anal. calcd. for C$_9$H$_{10}$N$_7$F$_3$O$_{18}$: C, 19.26, H, 1.80; N, 17.47; F, 10.16. Found: C, 19.35; H, 1.83; N, 17.20; F, 9.98.

EXAMPLE 8

5,5,5,Tris(2-fluoro-2,2-dinitroethoxy)-2,2-dinitro-4-oxapentanol (IX)

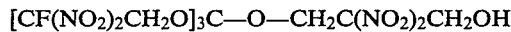
[CF(NO$_2$)$_2$CH$_2$O]$_3$C—O—CH$_2$C(NO$_2$)$_2$CH$_2$OH

Chlorine gas was passed into a solution of 6.53 g (0.01 mol) of tris(2-fluoro-2,2-dinitroethoxy)methyl trichloromethyl disulfide and 1.83 g (0.011 mol) of 2,2-dinitropropane-1,3-diol in 20 ml of dry 1,2-dichloroethane at 60°-65° C. for two hours. Heating at 60°-65° C. was continued for five hours before the volatiles were removed with a stream of nitrogen and the residual oil was washed with 2×10 ml of hexane. Addition of 20 ml of chloroform gave 5.90 g of solid (mp 71°-75° C.) which was stirred with 30 ml of water to yield 5.66 g (89 percent), mp 74-78 C. Crystallization from dichloroethane-chloroform gave 4.42 g, mp 79°-82° C.; H-NMR (CD$_2$Cl$_2$): δ 4.74 (d), 4.58 (s), 4.52 (s). IR (CH$_2$Cl$_2$ solution): 3590 (OH), 1605, 1580 (NO$_2$) cm$^{-1}$.

Anal. calculated for C$_{10}$H$_{11}$N$_8$F$_3$O$_{21}$: C, 18.88; H, 1.74; N, 17.61; F, 8.96. Found: C, 18.84; H, 1.73; N, 17.36; F, 9.20.

EXAMPLE 9

1,1,1,7,7,7-Hexakis(2-fluoro-2,2-dinitroethoxy)-4,4-dinitro-2,6-dioxaheptane (X)

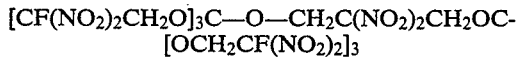
[CF(NO$_2$)$_2$CH$_2$O]$_3$C—O—CH$_2$C(NO$_2$)$_2$CH$_2$OC-[OCH$_2$CF(NO$_2$)$_2$]$_3$ A solution of 6.53 g (0.01 mol) of tris(2-fluoro-2,2-dinitroethoxy)methyl trichloromethyl disulfide and 0.83 g (0.005 mol) of 2,2-dinitropropane-1,3-diol in 20 ml of dry 1,2-dichloroethane was chlorinated for 2.5 hours at 60°-65° C. Heating at 60°-65° C. was continued for four days at which time solvent was removed with a stream of nitrogen until solid began to precipitate from the warm solution. Cooling in ice gave 3.48 g (63 percent) of a solid (mp 132°-134° C.) which was recrystallized from dichloroethane to give mp 133°-134.5° C.; H-NMR [(CD$_3$)$_2$C=O]: δ 5.17 (d), 4.92 (s); IR (KBr): no OH absorption; 1610, 1580 (NO$_2$) cm$^{-1}$.

Anal. calculated for C$_{17}$H$_{16}$N$_{14}$F$_6$O$_{36}$: C, 18.45; H, 1.46; N, 17.72; F, 10.30. Found: C, 18.47; H, 1.48; N, 17.65, F, 10.19.

EXAMPLE 10

11,11,11-Tris(2-fluoro-2,2-dinitroethoxy)-2,2,8,8-tetranitro-4,6,10-trioxaundecanol (XI)

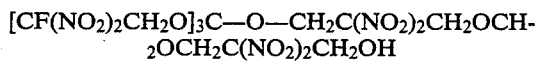
[CF(NO$_2$)$_2$CH$_2$O]$_3$C—O—CH$_2$C(NO$_2$)$_2$CH$_2$OCH$_2$OCH$_2$C(NO$_2$)$_2$CH$_2$OH Chlorine gas was passed into a solution of 3.78 g (0.011 mol) of 2,2,8,8-tetranitro-4,6-dioxanonane-1,9-diol and 6.53 g (0.01 mol) of tris(2-fluoro-2,2-dinitroethoxy)methyl trichloromethyl disulfide in 20 ml of dry 1,2-dichloroethane at 65° C. for two hours. Heating at 65° C. was continued for 22 hours at which time the solvent was removed and the oily residue was washed with 2×30 ml of hexane. Thin layer chromatography indicated the product was a mixture of the mono-(XI) and the bis-orthocarbonate (XII). The mono-orthocarbonate (XI) was isolated by column chromatography (silica gel 60, methylene chloride-ethyl acetate (90:10) as eluent) as a viscous gummy oil; H-NMR [(CD$_3$)$_2$C=O]: δ 5.20 (d), 4.96 (s), 4.83 (s), 4.68 (s), 4.58 (s), 4.54 (s). IR (film on NaCl plate) 3600 (OH), 1600 (NO$_2$) cm$^{-1}$.

EXAMPLE 11

1,1,1,13,13,13-Hexakis(2-fluoro-2,2-dinitroethoxy)-4,4,10,10-tetranitro-2,6,8,12-tetraoxatridecane (XII)

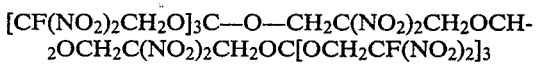
[CF(NO$_2$)$_2$CH$_2$O]$_3$C—O—CH$_2$C(NO$_2$)$_2$CH$_2$OCH$_2$OCH$_2$C(NO$_2$)$_2$CH$_2$OC[OCH$_2$CF(NO$_2$)$_2$]$_3$ A solution of 1.72 g (0.005 mol) of 2,2,8,8-tetranitro-4,6-dioxanonane-1,9-diol and 7.19 g (0.011 mol) of tris(2-fluoro-2,2-dinitroethoxy)methyl trichloromethyl disulfide in 20 ml of dry 1,2-dichloroethane was treated with chlorine gas at 65° C. for 2.5 hours and then held at 65° C. for a total of 30 hours. Most of the solvent was removed with a stream of nitrogen and the residue was washed with chloroform to give 6.15 g (96 percent) of a viscous oil. The product was dissolved in methylene chloride and chloroform was added to give a gum-like material (5.07 g, 79 percent) which thin-layer chromatography (TLC) showed to be essentially pure; H-NMR [(CD$_3$)$_2$C=O]: 5.20 (d, 12H), 4.98 (s, 2H), 4.81 (s, 4H), 4.67 (s, 4H); IR (film on NaCl plate): no OH absorption, 1600 (NO$_2$) cm$^{-1}$.

EXAMPLE 12

Tris(2-fluoro-2,2-dinitroethyl)(2,2,2-trifluoroethyl)orthocarbonate (XIII)

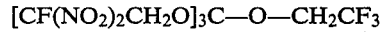
[CF(NO$_2$)$_2$CH$_2$O]$_3$C—O—CH$_2$CF$_3$

A solution of 6.5 g (0.01 mol) of tris(2-fluoro-2,2-dinitroethoxy)methyl trichloromethyl disulfide in 20 ml of dry 1,2 dichloroethane was treated with chlorine gas for five hours at ambient temperature. 2,2,2-trifluoroethanol (5 ml) was added and the solution was heated at reflux temperature for one hour before the solvent was removed and the residue was washed with hexane to give 5.57 g (98 percent), mp 55°-58° C. Recrystallization from chloroform gave 5.02 g, mp 57°-59° C.; H-NMR (CDCl$_3$): δ 4.75 (d), 3.99 (q).

Anal. calculated for C$_9$H$_8$N$_6$F$_6$O$_{16}$: C, 18.96; H, 1.41; N, 14.74; F, 19.99. Found: C, 19.05; H, 1.51; N, 14.50; F, 19.66

EXAMPLE 13

Tris(2-fluoro-2,2-dinitroethyl)(ethyl)orthocabonate (XIV)

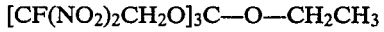
[CF(NO$_2$)$_2$CH$_2$O]$_3$C—O—CH$_2$CH$_3$

Tris(2-fluoro-2,2-dinitroethoxy)methyl trichloromethyl disulfide (6.53 g, 0.01 mol) in 20 ml of dry 1,2-dichloroethane was treated with chlorine gas for five hours at ambient temperature. The reaction solution was then gently heated as a stream of nitrogen was passed over it to remove excess chlorine and about 5 ml of solvent. Anhydrous ethanol (0.65 ml) was added and the solution was heated to reflux for one minute before most of the solvent was quickly removed with a stream of nitrogen. The oily residue was washed with 2×30 ml of hexanes, then was dried in a vacuum dessicator to give 4.55 g (88 percent) of an oil. Gas-liquid chromatography (GLC)analysis showed only one peak. HNMR (CDCl$_3$): δ 4.66 (d), 3.67 (q), 1.24 (t).

Anal. calculated for $C_9H_{11}N_6F_3O_{16}$: C, 20.94; H, 2.15; N, 16.28; F, 11.04. Found: C, 20.73; H, 1.99; N, 16.04; F, 10.81.

EXAMPLE 14

Tris(2-fluoro-2,2-dinitroethyl)2,3-epoxypropyl orthocarbonate (XV)

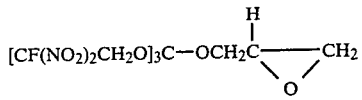

Chlorine gas was passed into a solution of 6.53 g (0.01 mol) of tris(2-fluoro-2,2-dinitroethoxy)methyl trichloromethyl disulfide in 20 ml of dry 1,2-dichloroethane at 60° for two hours. After an additional two hours at 60° the solvent was removed with a stream of nitrogen. The oily residue was stirred with hexane to give a solid which was washed twice with hexane before it was dissolved in 30 ml of dry dichlorethane. The solution was heated to 50° C. and 3 ml of 2,3-epoxy-1-propanol (glycidol) was added in one portion all at once. (The reaction solution was strongly purged with a stream of nitrogen to remove evolved hydrogen chloride and prevent its reaction with the epoxide). After approximately 15 minutes the solvent was removed and the residue was extracted with 2×50 ml of water to give 5.48 g of oil which was dissolved in 20 ml of chloroform. Hexane (6 ml) was added to the cloud point and the solution was filtered through a silica gel 60 pad and the pad was washed with methylene chloride. Removal of the solvent followed by crystallization from chloroform-hexane gave 4.4 g (81 percent), mp 51.5°-53° C.

H-NMR (CDCl$_3$): δ 4.71 (d), 4.00 (m), 3.38 (m), 3.14 (m), 2.89 (m), 2.63 (m).

Anal. calculated for $C_{10}H_{11}N_6F_3O_{17}$: C, 22.07; H, 2.04; N, 15.44; F, 10.47. Found: C, 22.06; H, 2.05; N, 15.27; F, 10.52

EXAMPLE 15

Trichloromethylsulfenic acid, 2-fluoro-2,2-dinitroethyl ester (XVIII)

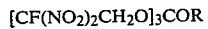

Perchloromethylmercaptan (5.6 g, 0.03 mol) and 2-fluoro-2,2-dinitroethanol (5.0 g, 0.033 mol) in 30 ml of methylene chloride was combined with 0.3 g of tetrabutyl ammonium chloride in 20 ml of water and the vigorously stirred mixture was cooled in an ice-salt bath. A solution obtained by diluting 2.6 g of 50 percent aqueous sodium hydroxide with 3 ml of water was added dropwise keeping the temperature at 0° C. Separation of the methylene chloride layer and removal of the solvent gave 8.2 g of an oil which was extracted with 2×40 ml of hexane. The combined extracts were passed through a silica gel 60 pad and the pad was washed with benzene. Removal of solvent gave 5.9 g (65 percent) of an oil which was essentially pure by TLC and GLC analysis; H-NMR (CDCl$_3$): δ 5.37 (d); mass spectrum (C.I.): m/e 304, 302, 267, 269.

Anal. calculated for $C_3H_2N_2Cl_3FSO_5$: C, 11.87; H, 0.66; N, 9.23; Cl, 35.05; F, 6.26; S, 10.56. Found: C, 11.85; H, 0.70; N, 9.05; Cl, 34.90; F, 6.14; S, 10.58.

To those skilled in the art, many modifications and variations of the present invention are possible in light of the above teachings. It is therefore to be understood that the present invention can be practiced otherwise than as specifically described herein and still be within the spirit and scope of the appended claims.

What is claimed is:

1. An orthocarbonate of the formula

[CF(NO$_2$)$_2$CH$_2$O]$_3$COR wherein R is selected from the group consisting of
—CH$_2$C(NO$_2$)$_3$,
—CH$_2$C(NO$_2$)$_2$CH$_3$,
—CH$_2$CH$_2$NO$_2$,
—CH$_2$C(NO$_2$)$_2$CH$_2$OH,
—CH$_2$C(NO$_2$)$_2$CH$_2$OC[OCH$_2$CF(NO$_2$)$_2$]$_3$,
—CH$_2$C(NO$_2$)$_2$CH$_2$OCH$_2$OCH$_2$C(NO$_2$)$_2$CH$_2$OH,
—CH$_2$C(NO$_2$)$_2$CH$_2$OCH$_2$OCH$_2$C(NO$_2$)$_2$CH$_2$OC[OCH$_2$CF(NO$_2$)$_2$]$_3$,
—CH$_2$CF$_3$, and
—CH$_2$CH$_3$.

2. The orthocarbonate of claim 1 which is tris(2-fluoro-2,2-dinitroethyl)(2,2,2-trinitroethyl)orthocarbonate.

3. The orthocarbonate of claim 1 which is tris(2-fluoro-2,2-dinitroethyl)(2,2-dinitropropyl)orthocarbonate.

4. The orthocarbonate of claim 1 which is tris(2-fluoro-2,2-dinitroethyl)(2-nitroethyl)orthocarbonate.

5. The orthocarbonate of claim 1 which is 5,5,5-tris(2-fluoro-2,2-dinitroethoxy)-2,2-dinitro-4-oxapentanol.

6. The orthocarbonate of claim 1 which is 1,1,1,7,7,7-hexakis(2-fluoro-2,2-dinitroethoxy)-4,4-dinitro-2,6-dioxaheptane.

7. The orthocarbonate of claim 1 which is 11,11,11-tris(2-fluoro-2,2-dinitroethoxy)-2,2,8,8-tetranitro-4,6,10-trioxaundecanol.

8. The orthocarbonate of claim 1 which is 1,1,1,13,13,13-hexakis(2-fluoro-2,2-dinitroethoxy)-4,4,10,10-tetranitro-2,6,8,12-tetraoxatridecane.

9. The orthocarbonate of claim 1 which is tris(2-fluoro-2,2-dinitroethyl)(2,2,2-trifluoroethyl)orthocarbonate.

10. The orthocarbonate of claim 1 which is tris(2-fluoro-2,2-dinitroethyl)(ethyl)orthocarbonate.

* * * * *